United States Patent
Akiyama et al.

(10) Patent No.: US 11,293,859 B2
(45) Date of Patent: Apr. 5, 2022

(54) FERMENTATION STATE MONITORING APPARATUS AND FERMENTATION STATE MONITORING METHOD

(71) Applicants: HAMAMATSU PHOTONICS K.K., Hamamatsu (JP); National Institute of Health Sciences, Kawasaki (JP)

(72) Inventors: Kouichiro Akiyama, Hamamatsu (JP); Kazuki Horita, Hamamatsu (JP); Hironori Takahashi, Hamamatsu (JP); Hiroshi Satozono, Hamamatsu (JP); Tomoaki Sakamoto, Kawasaki (JP)

(73) Assignees: HAMAMATSU PHOTONICS K.K., Hamamatsushi (JP); National Institute of Health Sciences, Kawasaki (JP)

( * ) Notice: Subject to any disclaimer, the term of this patent is extended or adjusted under 35 U.S.C. 154(b) by 0 days.

(21) Appl. No.: 16/701,242

(22) Filed: Dec. 3, 2019

(65) Prior Publication Data
US 2020/0173916 A1   Jun. 4, 2020

(30) Foreign Application Priority Data
Dec. 4, 2018   (JP) .............................. JP2018-227423

(51) Int. Cl.
*G01N 21/3581* (2014.01)
*G01N 21/55* (2014.01)
*G01N 33/02* (2006.01)

(52) U.S. Cl.
CPC ......... *G01N 21/3581* (2013.01); *G01N 21/55* (2013.01); *G01N 33/02* (2013.01)

(58) Field of Classification Search
CPC .... G01N 21/3581; G01N 21/55; G01N 33/02; G01N 21/3577; G01N 21/552
See application file for complete search history.

(56) References Cited

U.S. PATENT DOCUMENTS

| | | | |
|---|---|---|---|
| 2011/0081672 A1* | 4/2011 | Andersen | C12M 21/12 435/22 |
| 2014/0255566 A1* | 9/2014 | Cuomo | A23L 35/00 426/231 |
| 2018/0164209 A1* | 6/2018 | Stiens | G01N 22/04 |
| 2019/0357556 A1* | 11/2019 | Kashiwagi | C12R 1/225 |
| 2020/0096442 A1* | 3/2020 | Meyer | G01N 21/94 |

OTHER PUBLICATIONS

Tei, Kyoko et al., "Bio-monitoring of Yogurt Fermentation Process by Near Infrared Spectroscopy," Journal of the Japanese Society of Agricultural Machinery, 2007, vol. 69, No. 3, pp. 19-24, including partial English language translation.

\* cited by examiner

*Primary Examiner* — David P Porta
*Assistant Examiner* — Mamadou Faye
(74) *Attorney, Agent, or Firm* — Faegre Drinker Biddle & Reath LLP

(57) ABSTRACT

A fermentation state monitoring apparatus includes: a terahertz wave generation element that outputs inspection light using a terahertz wave to a fermented food under fermentation in a sealed product container; a terahertz wave detection element that detects return light of the inspection light reflected by the fermented food in the product container; and a determination unit that determines a fermentation progress of the fermented food based on an index value including a reflectance of the return light with respect to the inspection light or an absorption coefficient of the return light with respect to the inspection light.

12 Claims, 15 Drawing Sheets

FERMENTATION STATE MONITORING APPARATUS AND FERMENTATION STATE MONITORING METHOD

TECHNICAL FIELD

The present disclosure relates to a fermentation state monitoring apparatus and a fermentation state monitoring method.

BACKGROUND

For example, in yogurt produced by fermenting milk, it is known that as fermentation proceeds, lactose in milk is decomposed into lactic acid and accordingly a pH value in the liquid decreases from a state before fermentation. Even in an actual production site, a sample is extracted from the liquid under fermentation, and the progress of fermentation is inspected using a pH meter or the like. However, since such an inspection method corresponds to a destructive inspection, it is difficult to apply the inspection method to the total inspection of fermented foods under production.

As a method of inspecting fermented foods under production in a non-destructive manner, for example, a method described in Non Patent Literature 1 (Kyoko TEI, Aya NAKAO, Shoji NAKAMURA, "Bio-monitoring of Yogurt Fermentation Process by Near Infrared Spectroscopy", Journal of the Japanese Society of Agricultural Machinery (2007) Vol. 69, No. 3, pp. 19-24) can be mentioned. In Non Patent Literature 1, a technique for monitoring the yogurt fermentation process by the near-infrared spectroscopy is disclosed. In Non Patent Literature 1, focusing on the fact that components in milk change due to fermentation of milk and accordingly the offset of the absorption spectrum with respect to near-infrared light changes, it is shown that there is a correlation between offset change amount and pH by performing multivariate analysis of the offset change amount.

SUMMARY

However, in Non Patent Literature 1 mentioned above, it is only shown that there is a correlation between the offset change amount and the pH, and evaluation to the extent that the quality of fermentation can be determined by analyzing the behavior of fermented food under fermentation has not been made. In addition, depending on the type of fermented food, fermentation may be performed in a sealed product container made of paper or plastic. In this case, in the near-infrared spectroscopy, inspection light may not pass through the product container, and accordingly, it may be difficult to monitor the fermentation state in the product container.

The disclosure has been made in order to solve the aforementioned problem, and an object thereof is to provide a fermentation state monitoring apparatus and a fermentation state monitoring method capable of monitoring a fermentation state in a product container in a non-destructive manner.

A fermentation state monitoring apparatus according to an aspect of the disclosure includes: a terahertz wave output unit that outputs inspection light using a terahertz wave to a fermented food under fermentation in a sealed product container; a terahertz wave detection unit that detects return light of the inspection light reflected by the fermented food in the product container; and a determination unit that determines a fermentation progress of the fermented food based on an index value including a reflectance of the return light with respect to the inspection light or an absorption coefficient of the return light with respect to the inspection light.

In this fermentation state monitoring apparatus, a terahertz wave is output to the fermented food under fermentation in the sealed product container as inspection light. Since the terahertz wave passes through the product container made of, for example, paper or plastic, it is possible to inspect the fermented food in the product container in a non-destructive manner. In addition, the reflectance of the return light or the absorption coefficient of the return light has a correlation with the pH value of the fermented food under fermentation. Therefore, the fermentation progress of the fermented food can be determined in real time by using these parameters as index values.

In addition, a frequency of the terahertz wave may be 1 THz or less. In this frequency band, the transmission of the terahertz wave with respect to the product container made of paper or plastic can be sufficiently secured. In addition, since the correlation between the index value and the pH value is further strengthened, it is possible to improve the determination accuracy of the fermentation progress.

In addition, the determination unit may have a first index threshold value for the index value and a first time threshold value for an elapsed time from start of fermentation. When the elapsed time from the start of fermentation reaches the first time threshold value, in a case where the index value has not decreased from a value at the start of fermentation to the first index threshold value, the determination unit may determine that there is an abnormality in a fermentation state of the fermented food. In this manner, an abnormality in the fermentation state in the early stage of fermentation can be determined.

In addition, the determination unit may have a second index threshold value set to a value lower than the first index threshold value and a second time threshold value set to a time later than the first time threshold value. In a case where a time when the index value has decreased to the second index threshold value exceeds the second time threshold value, the determination unit may determine that there is an abnormality in the fermentation state of the fermented food. In this manner, an abnormality in the fermentation state in the late stage of fermentation can be determined.

In addition, the determination unit may store a first time when the index value has decreased to the first index threshold value and a second time when the index value has decreased to the second index threshold value. In a case where an inclination of a decrease in the index value between the first time and the second time is not in a predetermined range, the determination unit may determine that there is an abnormality in the fermentation state of the fermented food. In this manner, an abnormality in the progress of the fermentation state can be determined.

In addition, the terahertz wave detection unit may have a first detection unit that detects the return light, a second detection unit that detects a part of the inspection light, and a difference detection unit that detects a difference between a detection signal from the first detection unit and a detection signal from the second detection unit. In this case, since the influence of the output drift of the terahertz wave by the terahertz wave output unit can be eliminated, it is possible to improve the determination accuracy of the fermentation progress.

In addition, the fermentation state monitoring apparatus may further include an inspection head that guides the inspection light toward the fermented food. In this case, only the inspection head can be disposed close to the fermented food placed in a fermentation room or the like. Therefore, it is possible to secure good workability in the case of monitoring a large number of fermented foods and the like.

In addition, a fermentation state monitoring method according to another aspect of the disclosure includes: an output step for outputting inspection light using a terahertz wave to a fermented food under fermentation in a sealed product container; a detection step for detecting return light of the inspection light reflected by the fermented food in the product container; and a determination step for determining a fermentation progress of the fermented food based on an index value including a reflectance of the return light with respect to the inspection light or an absorption coefficient of the return light with respect to the inspection light.

In this fermentation state monitoring method, a terahertz wave is output to the fermented food under fermentation in the sealed product container as inspection light. Since the terahertz wave passes through the product container made of, for example, paper or plastic, it is possible to inspect the fermented food in the product container in a non-destructive manner. In addition, the reflectance of the return light or the absorption coefficient of the return light has a correlation with the pH value of the fermented food under fermentation. Therefore, the fermentation progress of the fermented food can be determined in real time by using these parameters as index values.

In addition, a frequency of the terahertz wave may be 1 THz or less. In this frequency band, the transmission of the terahertz wave with respect to the product container made of paper or plastic can be sufficiently secured. In addition, since the correlation between the index value and the pH value is further strengthened, it is possible to improve the determination accuracy of the fermentation progress.

In addition, in the determination step, a first index threshold value for the index value and a first time threshold value for an elapsed time from start of fermentation may be used. When the elapsed time from the start of fermentation reaches the first time threshold value, in a case where the index value has not decreased from a value at the start of fermentation to the first index threshold value, it may be determined that there is an abnormality in a fermentation state of the fermented food. In this manner, an abnormality in the fermentation state in the early stage of fermentation can be determined.

In addition, in the determination step, a second index threshold value set to a value lower than the first index threshold value and a second time threshold value set to a time later than the first time threshold value may be used. In a case where a time when the index value has decreased to the second index threshold value exceeds the second time threshold value, it may be determined that there is an abnormality in the fermentation state of the fermented food. In this manner, an abnormality in the fermentation state in the late stage of fermentation can be determined.

In addition, in the determination step, a first time when the index value has decreased to the first index threshold value and a second time when the index value has decreased to the second index threshold value may be stored. In a case where an inclination of a decrease in the index value between the first time and the second time is not in a predetermined range, it may be determined that there is an abnormality in the fermentation state of the fermented food. In this manner, an abnormality in the progress of the fermentation state can be determined.

In addition, in the detection step, detection of the return light and detection of a part of the inspection light may be performed, and a difference between a detection result of the return light and a detection result of a part of the inspection light may be detected. In this case, since the influence of the output drift of the terahertz wave by the terahertz wave output unit can be eliminated, it is possible to improve the determination accuracy of the fermentation progress.

In addition, in the output step and the detection step, an inspection head that guides the inspection light toward the fermented food may be used. In this case, only the inspection head can be disposed close to the fermented food placed in a fermentation room or the like. Therefore, it is possible to secure good workability in the case of monitoring a large number of fermented foods and the like.

DETAILED DESCRIPTION

Hereinafter, preferred embodiments of a fermentation state monitoring apparatus and a fermentation state monitoring method according to one aspect of the disclosure will be described in detail with reference to the diagrams.

[Overall Configuration of Fermentation State Monitoring Apparatus]

Figure 1:
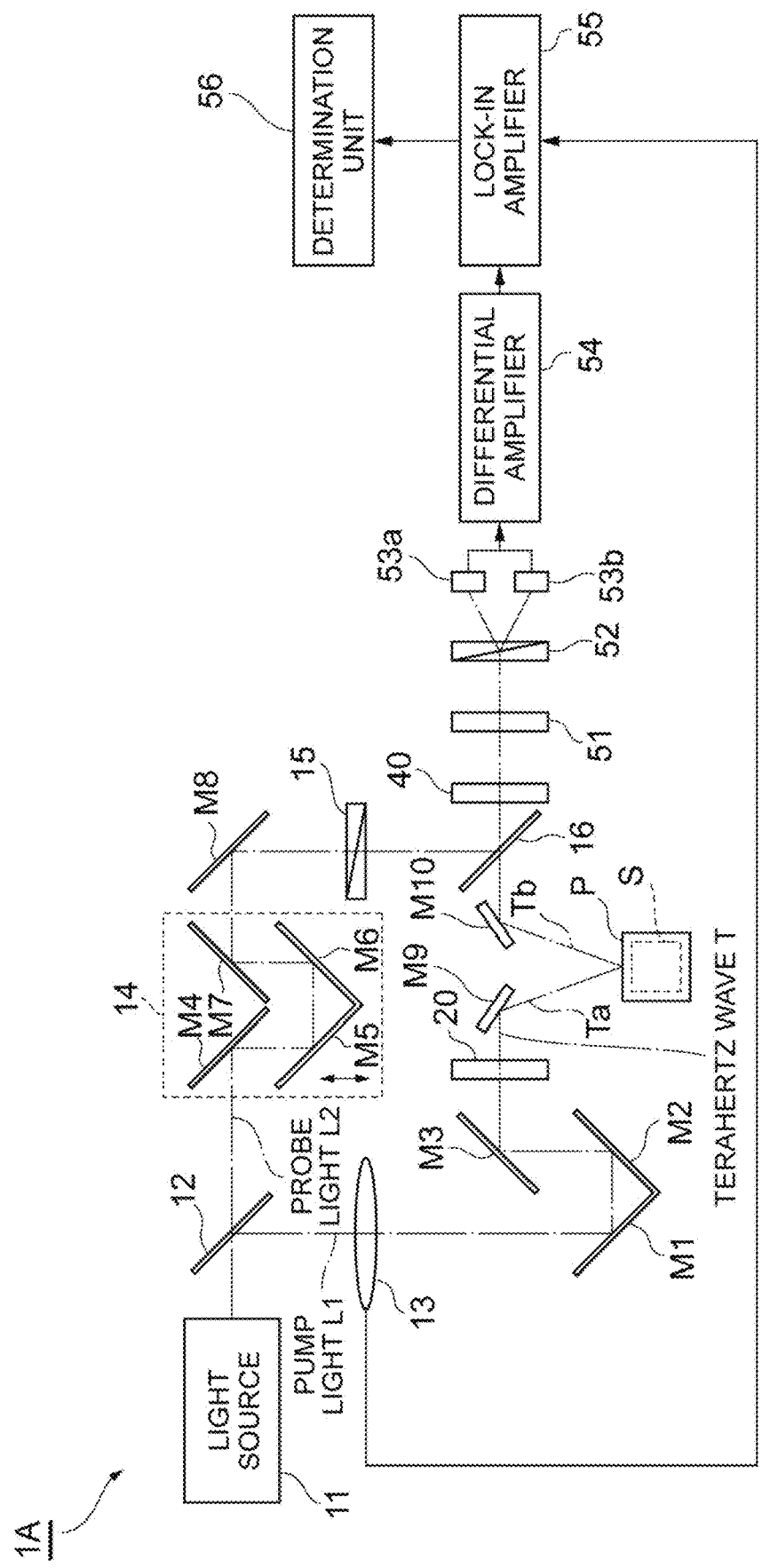
FIG. 1 is a schematic configuration diagram illustrating an example of a fermentation state monitoring apparatus.

FIG. 1 is a schematic configuration diagram illustrating an example of a fermentation state monitoring apparatus. A fermentation state monitoring apparatus 1A is configured as an apparatus that determines the fermentation progress of a fermented food S under fermentation in a sealed product container P in a non-destructive manner using a terahertz wave T. As the fermented food S to which the fermentation state monitoring apparatus 1A is applied, for example, yoghurt, soy sauce, miso, sake, cheese, bread, and the like can be mentioned. In the following description, a case where the fermented food S is yogurt is illustrated.

Generally, in producing yogurt, first, raw milk is prepared and sterilized, and lactic acid bacteria are added. Then, the raw milk to which lactic acid bacteria are added is filled in a sealed product container, packaging of the product container is performed, and then the raw milk is fermented in a fermentation room where the temperature is kept constant. After performing fermentation for about 4 to 6 hours in the fermentation room, it is confirmed that the acidity has increased to about 0.7% to 0.8%, and the fermentation is ended. In yogurt, it is known that as fermentation proceeds, lactose in milk is decomposed into lactic acid and accordingly the pH value in the liquid decreases from the state before fermentation. The fermentation state monitoring apparatus 1A is configured based on the knowledge that the reflectance of the terahertz wave T has a correlation with the pH value of the fermented food S under fermentation, and determines the fermentation progress of the fermented food S by emitting the terahertz wave T to the fermented food S under fermentation in the product container P and measuring the reflectance of the terahertz wave T as an index value.

As illustrated in FIG. 1, the fermentation state monitoring apparatus 1A includes a light source 11, a branching unit 12, a chopper 13, an optical path length difference adjusting unit 14, a polarizer 15, a multiplexing unit 16, a terahertz wave generation element (terahertz wave output unit) 20, a terahertz wave detection element (terahertz wave detection unit) 40, a $\lambda/4$ wavelength plate 51, a polarization separation element 52, a photodetector 53a, a photodetector 53b, a differential amplifier 54, a lock-in amplifier 55, and a determination unit 56.

The light source 11 outputs pulsed light at a constant repetition period. More specifically, the light source 11 is a femtosecond pulsed laser light source that outputs pulsed laser light having a pulse width on the order of femtoseconds. The branching unit 12 is, for example, a beam splitter, and branches the pulsed light output from the light source 11, outputs one of the branched pulsed light beams to a mirror M1 as pump light L1, and outputs the other to a mirror M4 as probe light L2.

The chopper 13 is provided on the optical path of the pump light L1 between the branching unit 12 and the mirror M1, and alternately repeats passage and blocking of the pump light L1 at a constant period. The pump light L1 output from the branching unit 12 and transmitted through the chopper 13 is sequentially reflected by the mirrors M1 to M3 and input to the terahertz wave generation element 20.

The terahertz wave generation element 20 is an element that generates the terahertz wave T as a pulse by the input of the pump light L1. The terahertz wave generation element 20 is configured by, for example, a nonlinear optical crystal (for example, ZnTe), a photoconductive antenna element (for example, an optical switch using GaAs), a semiconductor (for example, InAs), or a superconductor. In a case where the terahertz wave generation element 20 is configured by a nonlinear optical crystal, the terahertz wave generation element 20 generates the terahertz wave T due to a nonlinear optical phenomenon that occurs as the pump light L1 is incident.

The terahertz wave T is an electromagnetic wave having a frequency of about 0.01 THz to 100 THz (in particular, about 0.1 THz to 10 THz) corresponding to an intermediate region between the light wave and the radio wave, and has an intermediate property between the light wave and the radio wave. In addition, terahertz waves are generated at a constant repetition period, and the pulse width is about several picoseconds. The terahertz wave T output from the terahertz wave generation element 20 is guided to the product container P as inspection light Ta by a mirror M9. The inspection light Ta is reflected at the interface of the fermented food S in the product container P to acquire optical information (here, the reflectance) of the fermented food S, and then becomes return light Tb. The return light Tb is reflected by a mirror M10 and guided to the multiplexing unit 16.

On the other hand, the probe light L2 output from the branching unit 12 is sequentially reflected by the mirrors M4 to M8, passes through the polarizer 15, and is input to the multiplexing unit 16. The four mirrors M4 to M7 configure the optical path length difference adjusting unit 14. That is, by moving the mirrors M5 and M6, the optical path length between the mirrors M4 and M7 and the mirrors M5 and M6 is adjusted, and the optical path length of the optical system of the probe light L2 is adjusted. That is, the optical path length difference adjusting unit 14 adjusts the difference between the optical path of the optical system of the pump light L1 and the terahertz wave T from the branching unit 12 to the multiplexing unit 16 and the optical path of the optical system of the probe light L2 from the branching unit 12 to the multiplexing unit 16.

The multiplexing unit 16 combines the return light Tb from the product container P and the probe light L2, and guides the return light Tb and the probe light L2 to the terahertz wave detection element 40 in a coaxial state. As the multiplexing unit 16, for example, a pellicle is used. The pellicle is a film-like mirror that is bonded to a solid support frame and stretched thinly.

The terahertz wave detection element 40 is an element that detects a correlation between the terahertz wave T and the probe light L2. In a case where the terahertz wave detection element 40 is configured by an electro-optic crystal, in the terahertz wave detection element 40, birefringence is induced by the Pockels effect as the terahertz wave T that is the return light Tb propagates. In addition, the polarization state of the probe light L2 changes due to birefringence. The amount of birefringence at this time depends on the electric field strength of the terahertz wave. Therefore, the amount of change in the polarization state of the probe light L2 in the terahertz wave detection element 40 depends on the electric field strength of the terahertz wave T.

The polarization separation element 52 is configured by, for example, a Wollaston prism. The polarization separation element 52 separates the probe light L2, which is output from the terahertz wave detection element 40 and transmitted through the $\lambda/4$ wavelength plate 51, into two polarization components perpendicular to each other. The photodetectors 53a and 53b are configured by, for example, photodiodes. The photodetectors 53a and 53b detect the power of the two polarization components of the probe light L2 polarized and separated by the polarization separation element 52, and output electric signals each having a value corresponding to the detected power to the differential amplifier 54.

The differential amplifier 54 receives the electric signal output from each of the photodetectors 53a and 53b, and outputs an electric signal having a value corresponding to the difference between the values of the two electric signals to the lock-in amplifier 55. The lock-in amplifier 55 synchronously detects the electric signal output from the differential amplifier 54 using the repetition frequency of the passage/blocking of the pump light L1 in the chopper 13 as a reference signal. The lock-in amplifier 55 outputs an electric signal having a value corresponding to the result of synchronization detection to the determination unit 56. The electric signal output from the lock-in amplifier 55 has a value that depends on the electric field strength of the terahertz wave T. By detecting the correlation between the terahertz wave T and the probe light L2 and detecting the electric field amplitude of the terahertz wave T, it is possible to obtain information of the reflectance of the fermented food S under fermentation with respect to the terahertz wave T.

The determination unit 56 is a unit that determines the fermentation progress of the fermented food S based on the index value. Physically, the determination unit 56 is configured by, for example, a computer system including a memory such as a RAM and a ROM, a processor such as a CPU, a communication interface, and a storage unit such as a hard disk. As such a computer, for example, a personal computer, a microcomputer, a cloud server, a smart device (a smart phone, a tablet terminal, and the like) can be mentioned. The determination unit 56 may be configured by an integrated circuit, such as a field-programmable gate array (FPGA). The operation of the determination unit 56 will be described later.

Figure 2:
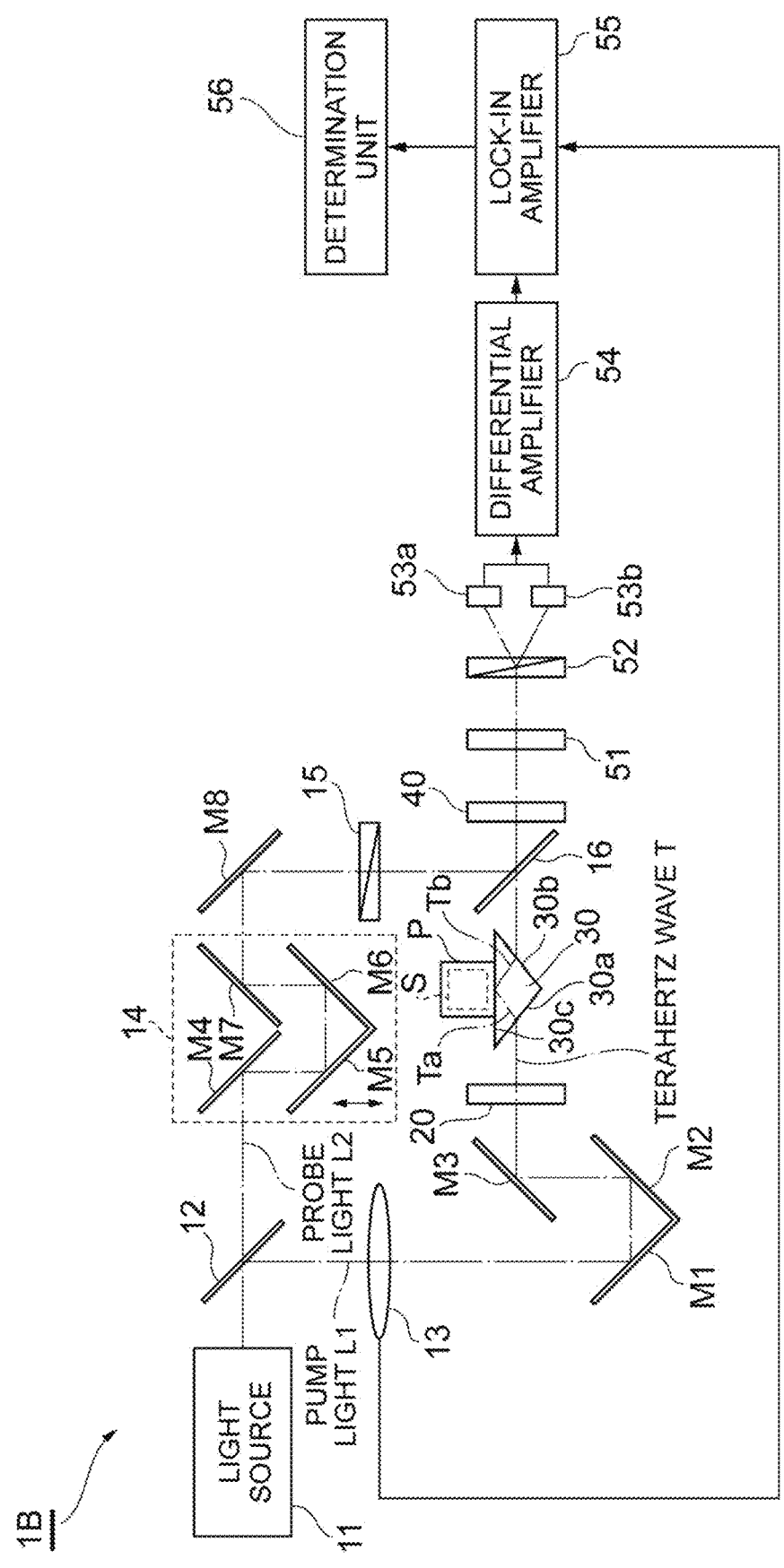
FIG. 2 is a schematic configuration diagram illustrating another example of a fermentation state monitoring apparatus.

In addition, FIG. 2 is a schematic configuration diagram illustrating another example of a fermentation state monitoring apparatus. A fermentation state monitoring apparatus 1B according to another example is configured based on the knowledge that an absorption coefficient of the terahertz wave T has a correlation with the pH value of the fermented food S under fermentation, and determines the fermentation progress of the fermented food S by emitting the terahertz wave T to the fermented food S under fermentation in the product container P and measuring the absorption coefficient of the terahertz wave T as an index value.

The fermentation state monitoring apparatus 1B is an apparatus to which a total reflection measurement method using the terahertz wave T is applied. The fermentation state monitoring apparatus 1B is the same as the form illustrated in FIG. 1 except that a prism 30 is provided on the optical path between the terahertz wave generation element 20 and the terahertz wave detection element 40 instead of the mirrors M9 and M10. The prism 30 has an incidence surface 30a to which the terahertz wave T output from the terahertz wave generation element 20 is input, a total reflection surface 30c that totally reflects the terahertz wave T input to the incidence surface 30a, and an emission surface 30b from which the terahertz wave T totally reflected by the total reflection surface 30c is output. The prism 30 is a Dach prism, and the optical axis of the terahertz wave T input to the incidence surface 30a and the optical axis of the terahertz wave T output from the emission surface 30b are located on a common straight line.

The outer surface side of the total reflection surface 30c of the prism 30 is an arrangement surface on which the product container P is disposed. The terahertz wave T incident from the incidence surface 30a propagates through the prism 30 as the inspection light Ta and is totally reflected by the total reflection surface 30c. At the time of total reflection, an evanescent component of the terahertz wave T is generated in the vicinity of the outer surface side of the total reflection surface 30c, and optical information (here, the absorption coefficient) of the fermented food S is acquired. The terahertz wave T totally reflected by the total reflection surface 30c becomes the return light Tb, propagates through the prism 30, is emitted from the emission surface 30b, and is guided to the multiplexing unit 16.

[Aspect of Emission of Inspection Light and Inspection Head]

Figure 3A:
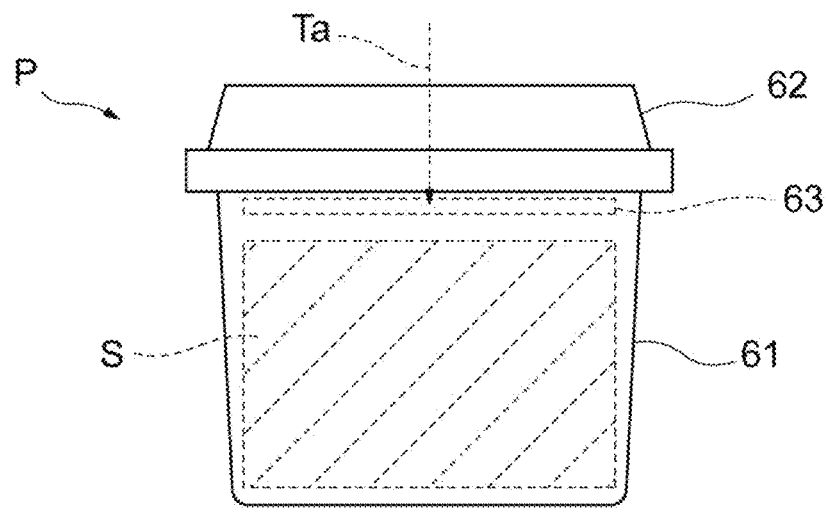
FIG. 3A is a diagram illustrating an aspect of emission of inspection light to a product container.
Figure 3B:
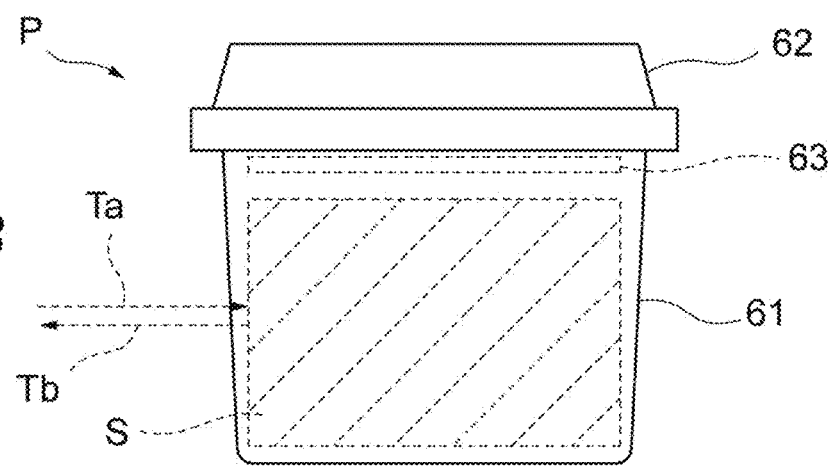
FIG. 3B is a diagram illustrating another example of the aspect of emission of inspection light to a product container.
Figure 3C:
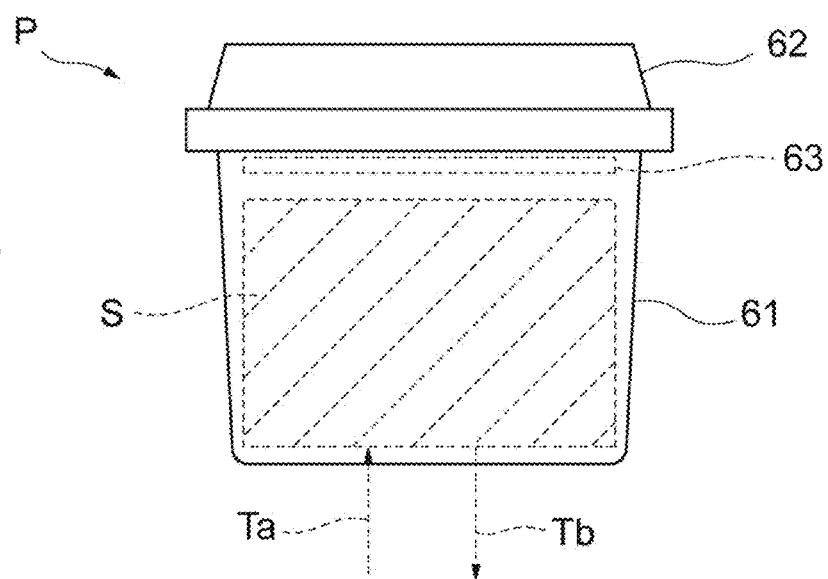
FIG. 3C is a diagram illustrating still another example of the aspect of emission of inspection light to a product container.

FIGS. 3A to 3C are diagrams illustrating an aspect of emission of inspection light to a product container. The product container P for yoghurt includes, for example, a bottomed main body unit 61 whose upper surface side is open and a lid unit 62 that fits to the upper portion of the main body unit 61. The main body unit 61 is made of, for example, paper or plastic, and is filled with raw milk under fermentation. In addition, an aluminum foil 63 for hermetically sealing the raw milk in the main body unit 61 is provided at the upper portion of the main body unit 61 so as to close the opening portion.

For this reason, as illustrated in FIG. 3A, when the inspection light Ta is emitted from the upper side of the product container P, it is conceivable that the inspection light Ta is blocked by the aluminum foil 63 and accordingly the inspection light Ta does not reach the raw milk to be monitored. Therefore, it is preferable to adopt an aspect in which the inspection light Ta is emitted from the lateral side of the product container P as illustrated in FIG. 3B or an aspect in which the inspection light Ta is emitted from the lower side of the product container P as illustrated in FIG. 3C. In addition, in a case where unevenness or the like is present on a part of the surface of the product container P, it is preferable to emit the inspection light Ta to a flat portion while avoiding the unevenness.

Figure 4:
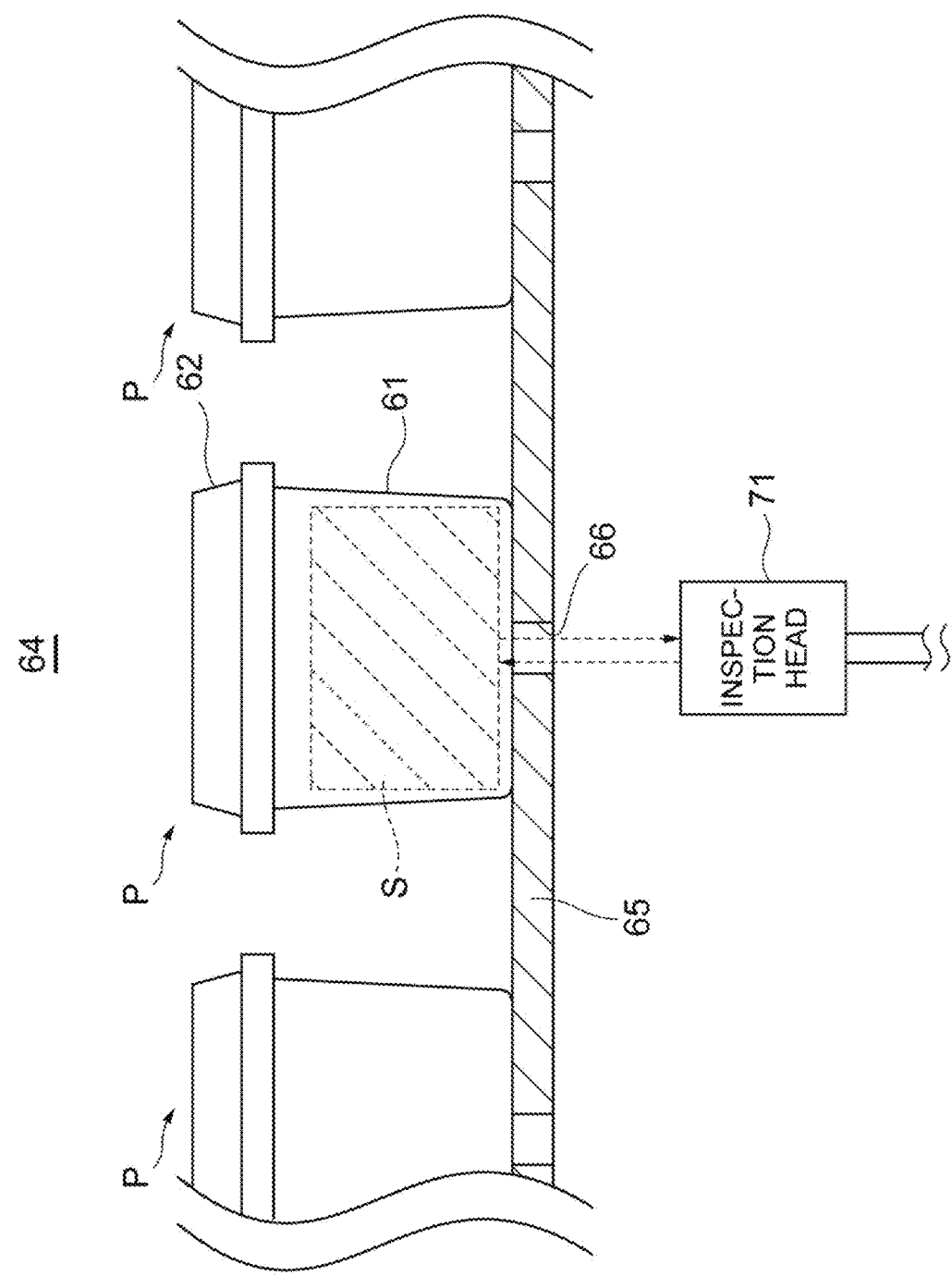
FIG. 4 is a diagram illustrating an example of the arrangement of an inspection head with respect to a product container.

In addition, for example, as illustrated in FIG. 4, in a case where a plurality of product containers P are arranged on a shelf 65 in a fermentation room 64, it is preferable to configure the fermentation state monitoring apparatuses 1A and 1B using an inspection head 71 that guides the inspection light Ta and the return light Tb and dispose the apparatus main body to the outside of the fermentation room 64 and introduce only the inspection head 71 into the fermentation room 64. In this case, at least a portion for guiding the inspection light Ta toward the fermented food S may be mounted in the inspection head 71.

In the fermentation state monitoring apparatuses 1A and 1B, for example, as illustrated in FIGS. 1 and 2, elements from the terahertz wave generation element 20 to the photodetectors 53a and 53b are disposed in the inspection head 71, and the other elements are disposed on the apparatus main body side. The inspection head 71 and the apparatus main body may be optically coupled using, for example, an optical fiber 72. In a case where the inspection head 71 is introduced into the fermentation room 64, as illustrated in FIG. 4, an opening 66 may be provided in the shelf 65, on which the product container P is placed, corresponding to the position of the product container P, and the emission of the inspection light Ta to the product container P and the detection of the return light Tb from the product container P may be sequentially performed through the opening 66 by using the inspection head 71 brought close to the opening 66.

[Correlation Between Index Value and Fermentation Progress]

Figure 5:
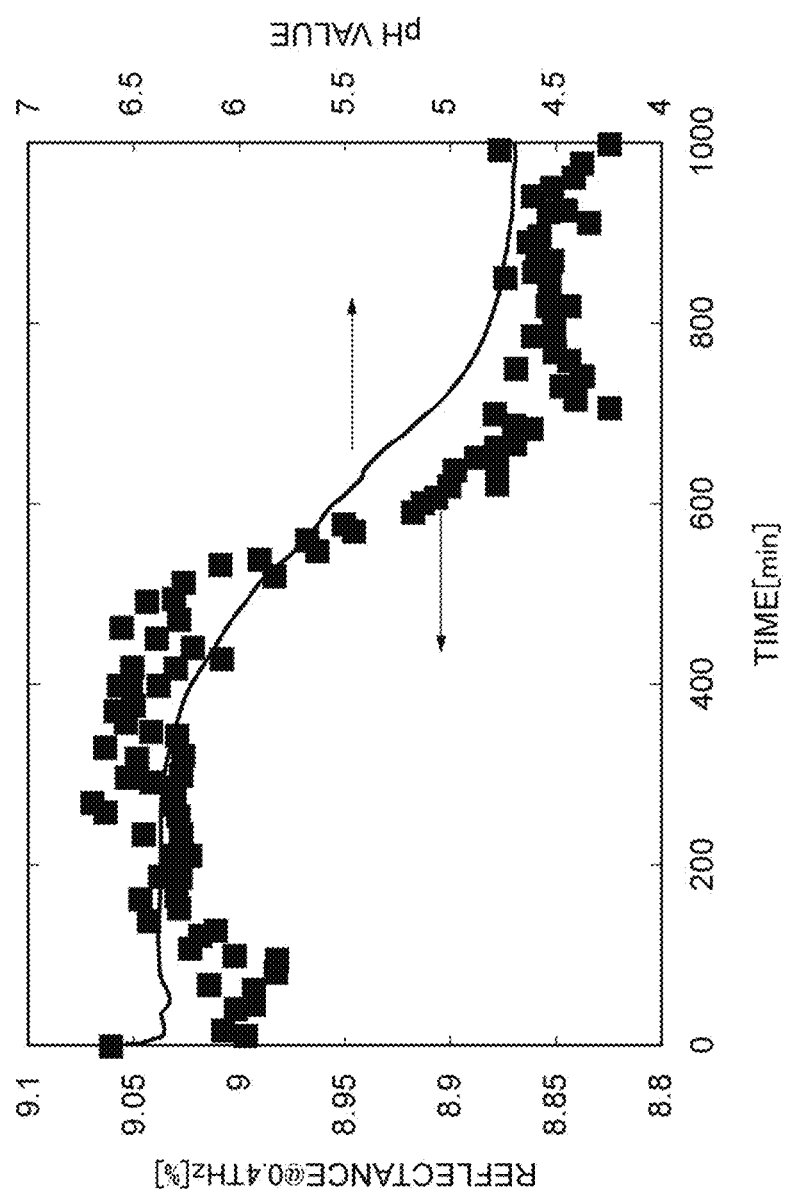
FIG. 5 is a graph showing a correlation between the reflectance of a terahertz wave and a pH value.

FIG. 5 is a graph showing a correlation between the reflectance of a terahertz wave and a pH value. In the example of FIG. 5, the horizontal axis indicates time (elapsed time from the start of fermentation), the left vertical axis indicates the reflectance of the fermented food S with respect to the terahertz wave T, and the right vertical axis indicates the pH value of the fermented food S. As the behavior of the fermentation progress, in the example of FIG. 5, until around 400 minutes from the start of fermentation, lactic acid bacteria added to raw milk gradually increase and the pH value is approximately constant at about 6.0 to 6.5. In the vicinity of 400 minutes to 800 minutes from the start of fermentation, the increase in lactic acid bacteria accelerates, and the pH value decreases with an approximately constant inclination from about 6.0 to about 4.8. After 800 minutes, the activity of lactic acid bacteria is weakened due to a decrease in the pH value, and almost no change in pH value is observed.

In the graph of FIG. 5, the value of the reflectance is measured using the terahertz wave T having a frequency of 0.4 THz. As shown in FIG. 5, the change in the value of the reflectance follows the change in the pH value of the fermented food S. That is, the reflectance is approximately constant at about 9% to 9.05% until around 400 minutes from the start of fermentation, and decreases with an approximately constant inclination from about 9% to about 8.9% in the vicinity of 400 minutes to 800 minutes from the start of fermentation. After 800 minutes, almost no change in reflectance is observed.

Figure 6:
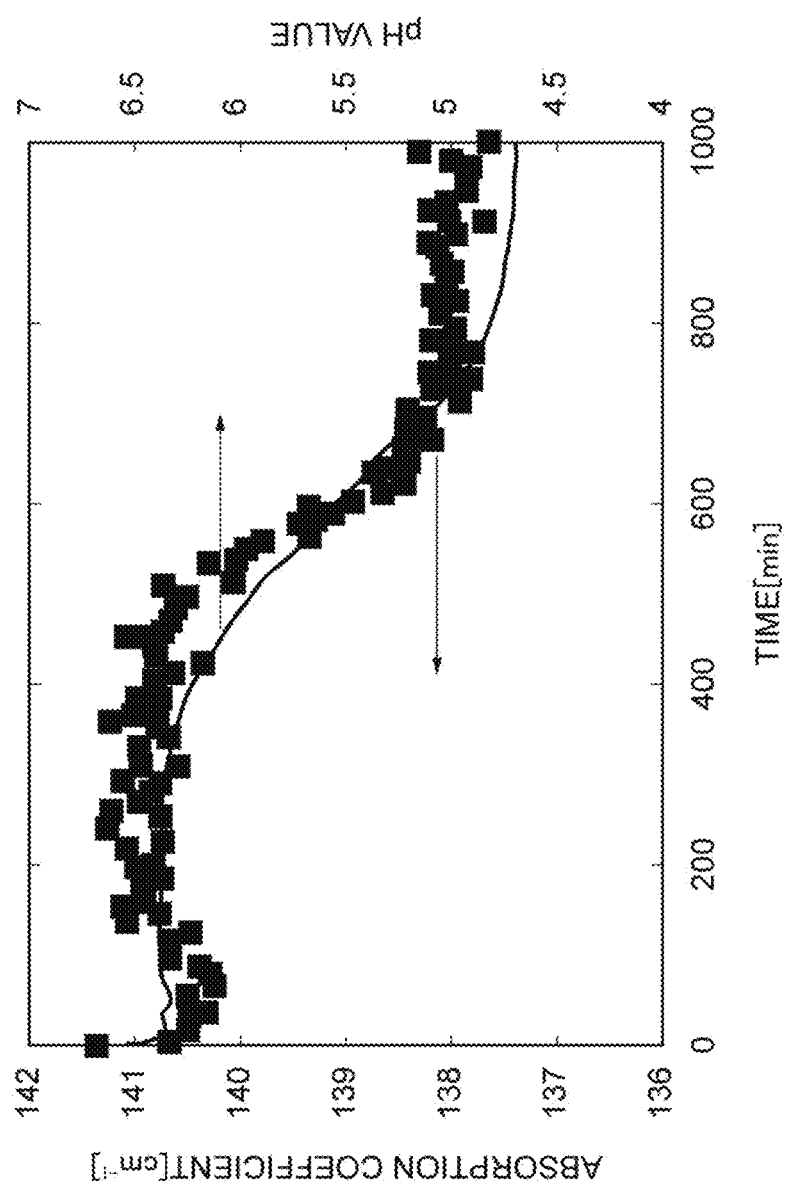
FIG. 6 is a graph showing a correlation between an absorption coefficient of a terahertz wave and a pH value.
Figure 7:
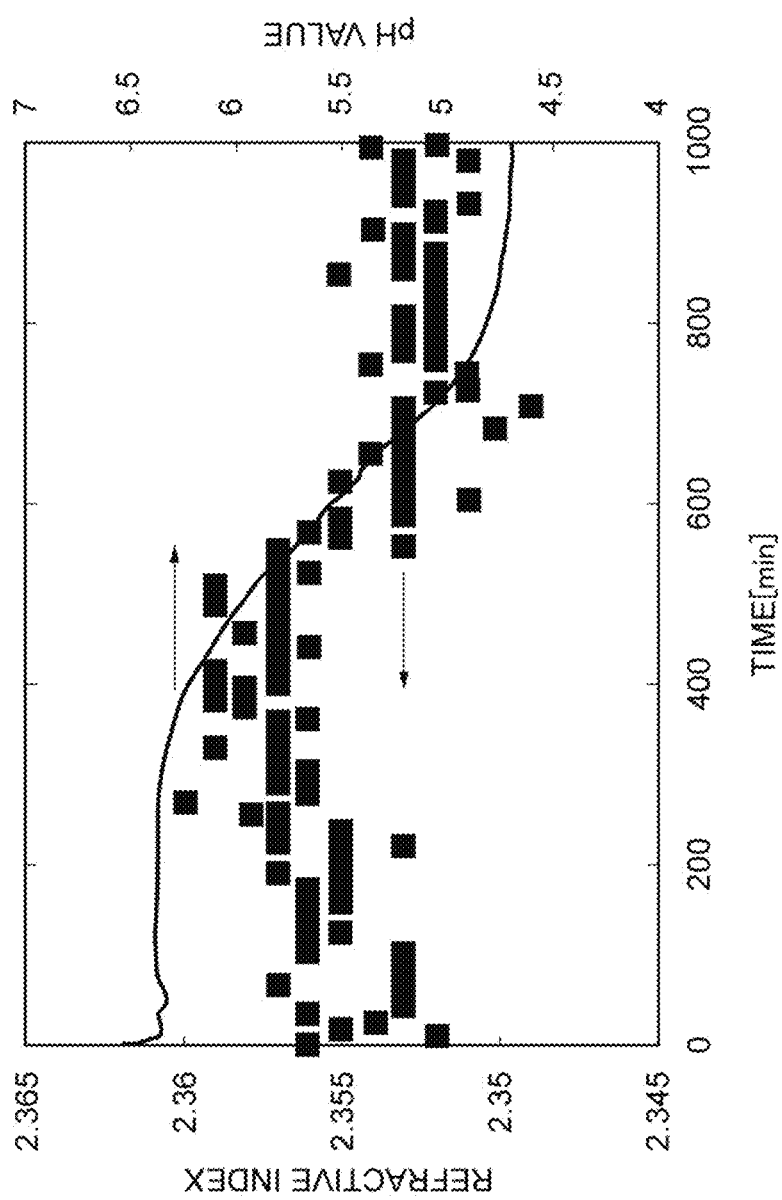
FIG. 7 is a graph showing a correlation between the refractive index of a terahertz wave and a pH value.

Such a correlation is the same even in a case where the absorption coefficient is used as an index value. In a case where the total reflection type measurement is performed as in the fermentation state monitoring apparatus 1B illustrated in FIG. 2, it is possible to acquire information of the phase shift and the reflectance of the fermented food S that is a sample. Based on the values of the acquired reflectance and phase shift, the absorption coefficient and the refractive index of the fermented food S can be calculated. FIG. 6 is a graph showing a correlation between an absorption coefficient of a terahertz wave and a pH value. Also in the example of FIG. 6, the absorption coefficient is approximately constant at about 140 $cm^{-1}$ to 141 $cm^{-1}$ until around 400 minutes from the start of fermentation, and decreases with an approximately constant inclination from about 140 $cm^{-1}$ to about 137.5 $cm^{-1}$ in the vicinity of 400 minutes to 800 minutes from the start of fermentation. After 800 minutes, almost no change in absorption coefficient is observed. In addition, as shown in FIG. 7, instead of the reflectance, a refractive index can also be used as an index value. In this case, after calculating the reflectance of the terahertz wave T, the refractive index may be calculated from the calculated reflectance.

In addition, it is preferable that the frequency of the terahertz wave T used in the fermentation state monitoring apparatuses 1A and 1B is a low frequency. When the transmittance of an actual product container for yoghurt was measured while changing the frequency of the terahertz wave, almost no terahertz wave absorption was observed up to about 5 THz in a product container made of plastic. On the other hand, in a product container made of paper, a result was obtained that the absorption of terahertz waves increased as moving to the high frequency band and the absorption coefficient was about 20 $cm^1$ at 1 THz, whereas the absorption coefficient reached 30 to 40 $cm^{-1}$ at 1.5 THz.

Figure 8:
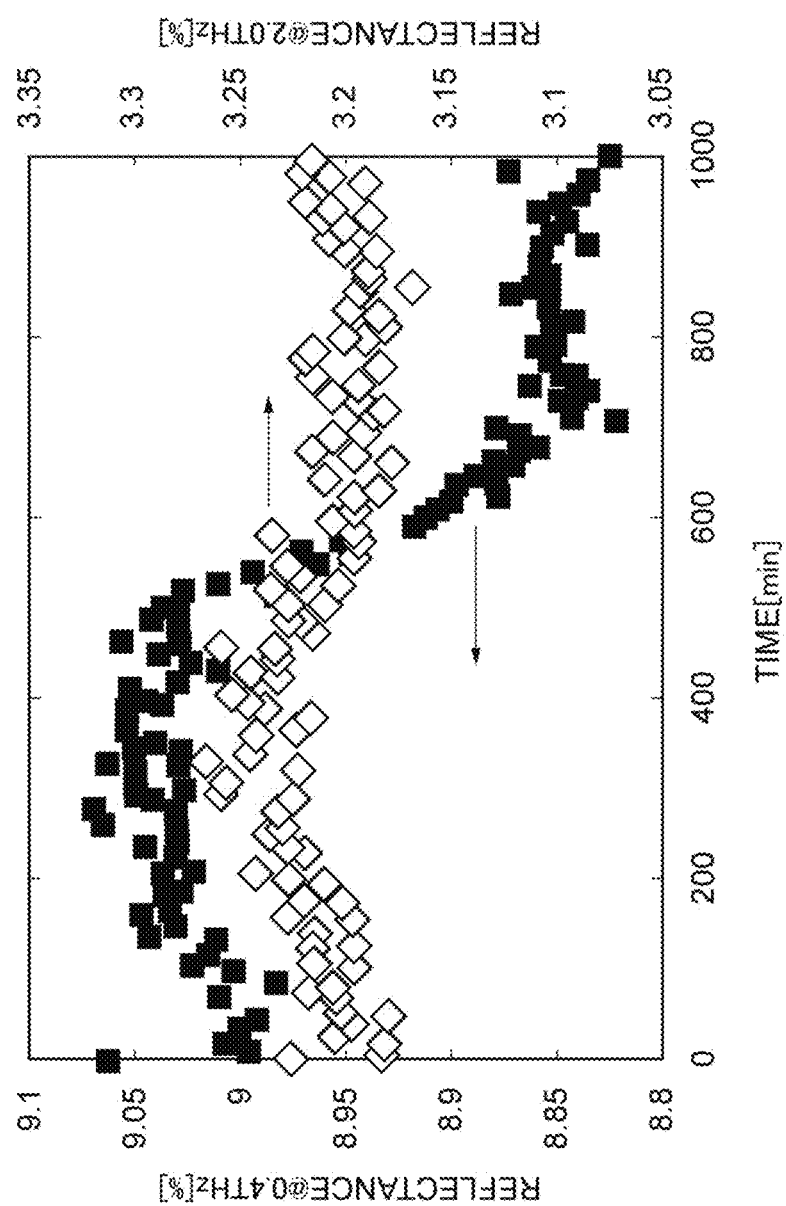
FIG. 8 is a graph showing the strength of a correlation between the reflectance and the pH value according to a difference in the frequency of the terahertz wave.

In addition, the difference in the frequency of the terahertz wave T also influences the strength of the correlation between the index value and the pH value. FIG. 8 is a graph showing the strength of the correlation between the reflectance and the pH value according to the difference in the frequency of the terahertz wave. In the example of FIG. 8, the horizontal axis indicates time (elapsed time from the start of fermentation), the left vertical axis indicates a reflectance in a case where the terahertz wave T having a frequency of 0.4 THz is used, and the right vertical axis indicates a reflectance in a case where the terahertz wave T having a frequency of 2.0 THz is used. The reflectance plot ranges on the left and right vertical axes were both 0.3%. As can be seen from FIG. 8, the amount of change in reflectance with respect to the amount of change in pH value in a case where the terahertz wave having a frequency of 0.4 THz is used is larger than that in a case where the terahertz wave having a frequency of 2.0 THz is used. Therefore, it can be seen that there is a strong correlation between the index value and the pH value in a case where the terahertz wave having a frequency of 0.4 THz is used.

Figure 9:
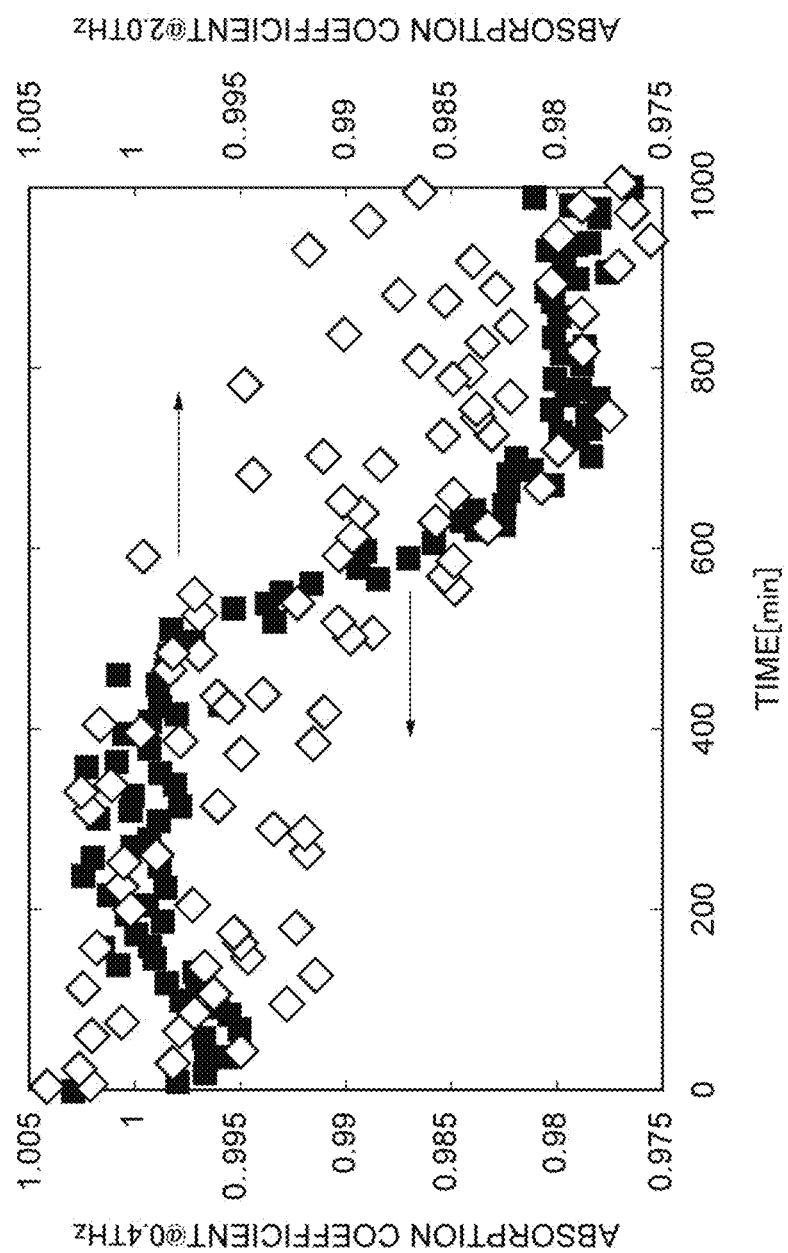
FIG. 9 is a graph showing the strength of a correlation between the absorption coefficient and the pH value according to a difference in the frequency of the terahertz wave.
Figure 10:
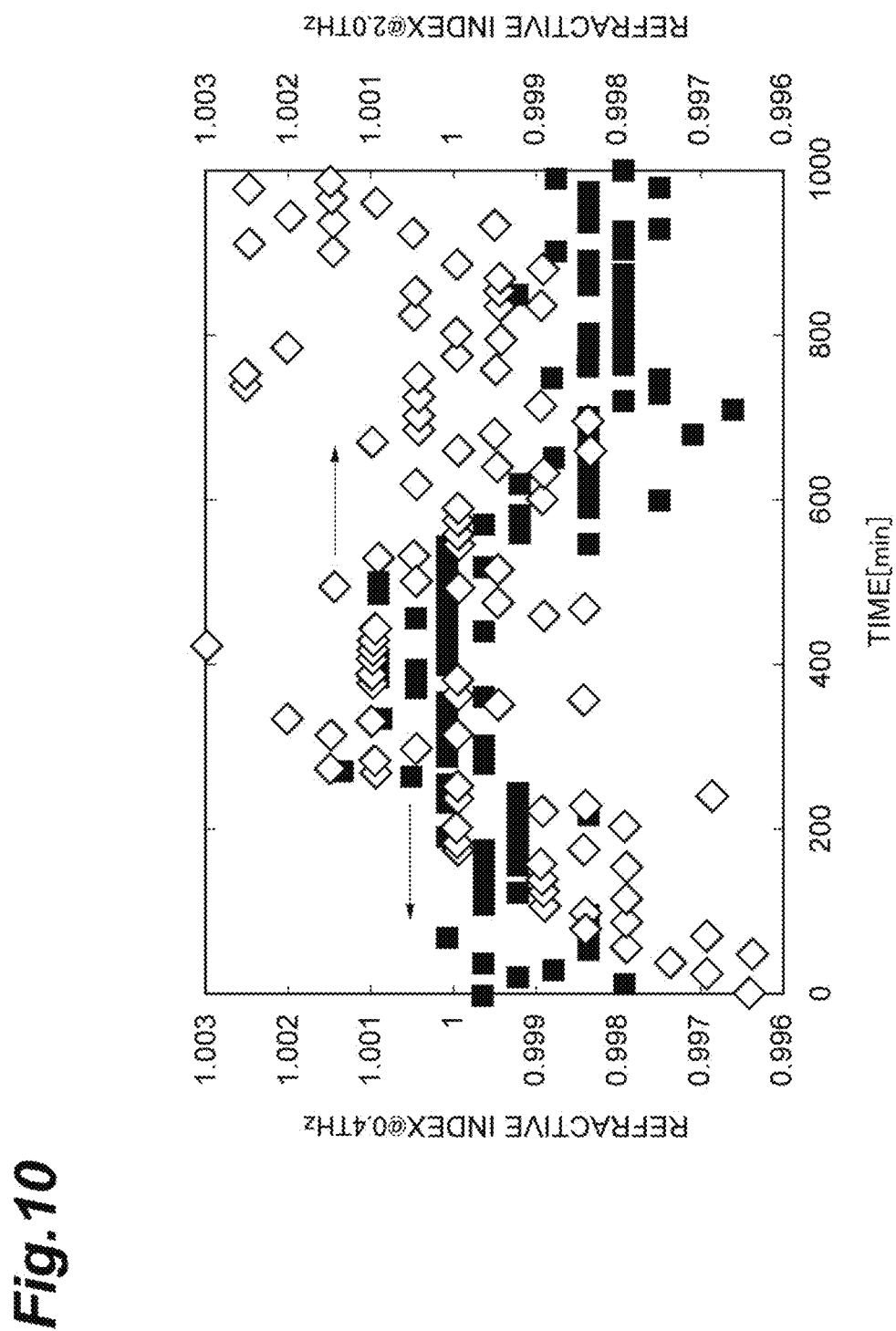
FIG. 10 is a graph showing the strength of a correlation between the refractive index and the pH value according to a difference in the frequency of the terahertz wave.

This is the same even in a case where the absorption coefficient and the refractive index are used as index values. FIG. 9 is a graph showing the strength of the correlation between the absorption coefficient and the pH value according to the difference in the frequency of the terahertz wave. In addition, FIG. 10 is a graph showing the strength of the correlation between the refractive index and the pH value according to the difference in the frequency of the terahertz wave. In the examples of FIGS. 9 and 10, data in the range of 200 minutes to 400 minutes is averaged, and a value normalized by the average value is shown on the vertical axis. From FIGS. 9 and 10, it can also be seen that the amount of change in each of the absorption coefficient and the refractive index with respect to the amount of change in the pH value in a case where the terahertz wave having a frequency of 0.4 THz is used is larger than that in a case where the terahertz wave having a frequency of 2.0 THz is used, and accordingly, there is a strong correlation between the index value and the pH value in a case where the terahertz wave having a frequency of 0.4 THz is used. As described above, considering the transmission with respect to the product container P and the strength of the correlation between the index value and the pH value, it can be concluded that the frequency of the terahertz wave T is preferably 2.0 THz or less, and more preferably 1 THz or less.

[Determination of Fermentation Progress by Determination Unit]

Figure 11:
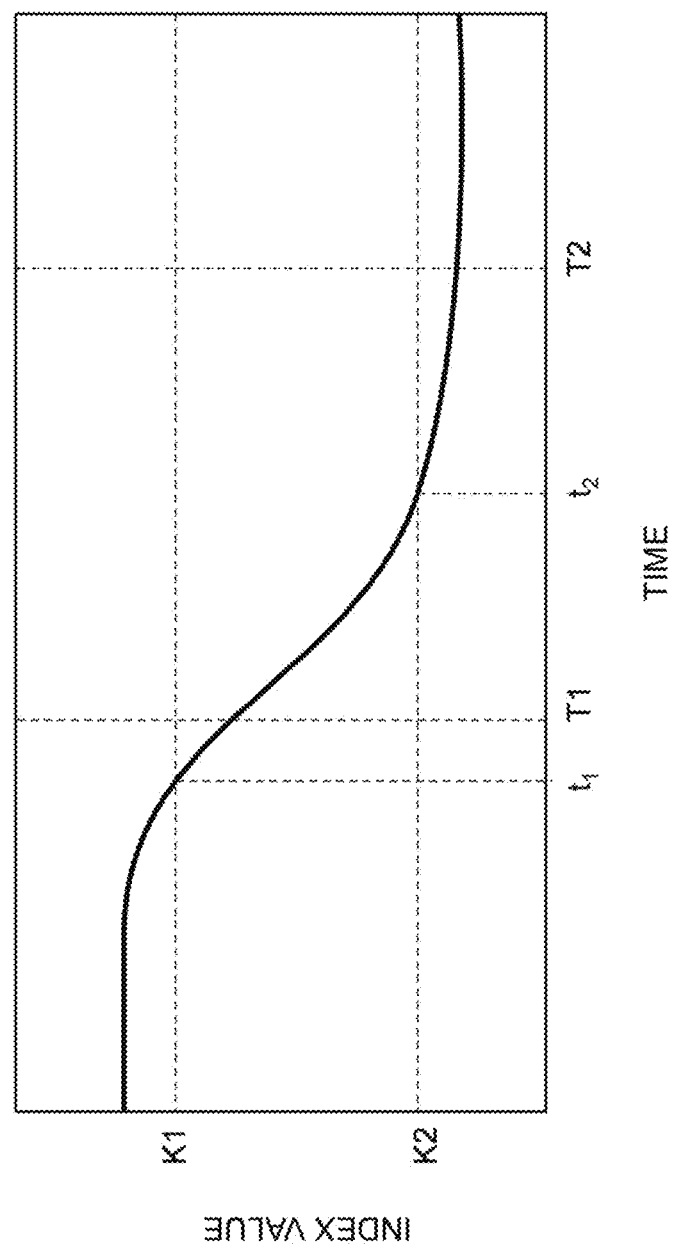
FIG. 11 is a diagram illustrating an example of setting threshold values used for determination of the fermentation progress.

FIG. 11 is a diagram illustrating an example of setting threshold values used for determination of the fermentation progress. As illustrated in FIG. 11, the determination unit 56 has a first index threshold value K1 and a second index threshold value K2 for the index value and a first time threshold value T1 and a second time threshold value T2 for the elapsed time from the start of fermentation. These threshold values are set based on the measurement results obtained by measuring a change in index value in a case where fermentation of a fermented food is performed normally multiple times, for example.

The first index threshold value K1 and the first time threshold value T1 are threshold values for the time when an increase in lactic acid bacteria accelerates and the index value at that time. The second index threshold value K2 and the second time threshold value T2 are threshold values for the time when the activity of lactic acid bacteria is weakened and the fermentation ends and the index value at that time.

The second index threshold value K2 is set to a value lower than the first index threshold value K1, and the second time threshold value T2 is set to a time later than the first time threshold value T1.

Figure 12:
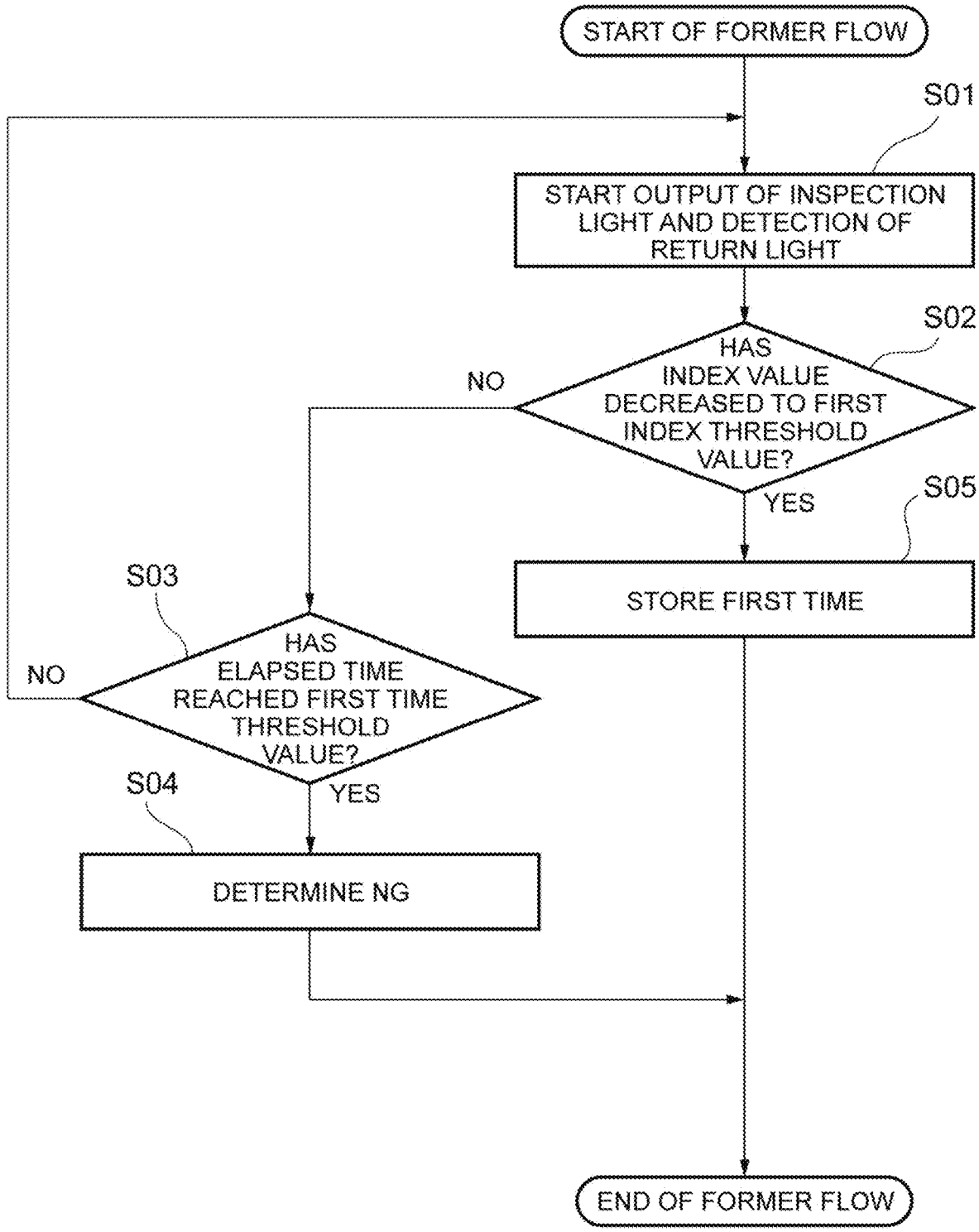
FIG. 12 is a diagram illustrating an example of a former flow of determination.
Figure 13:
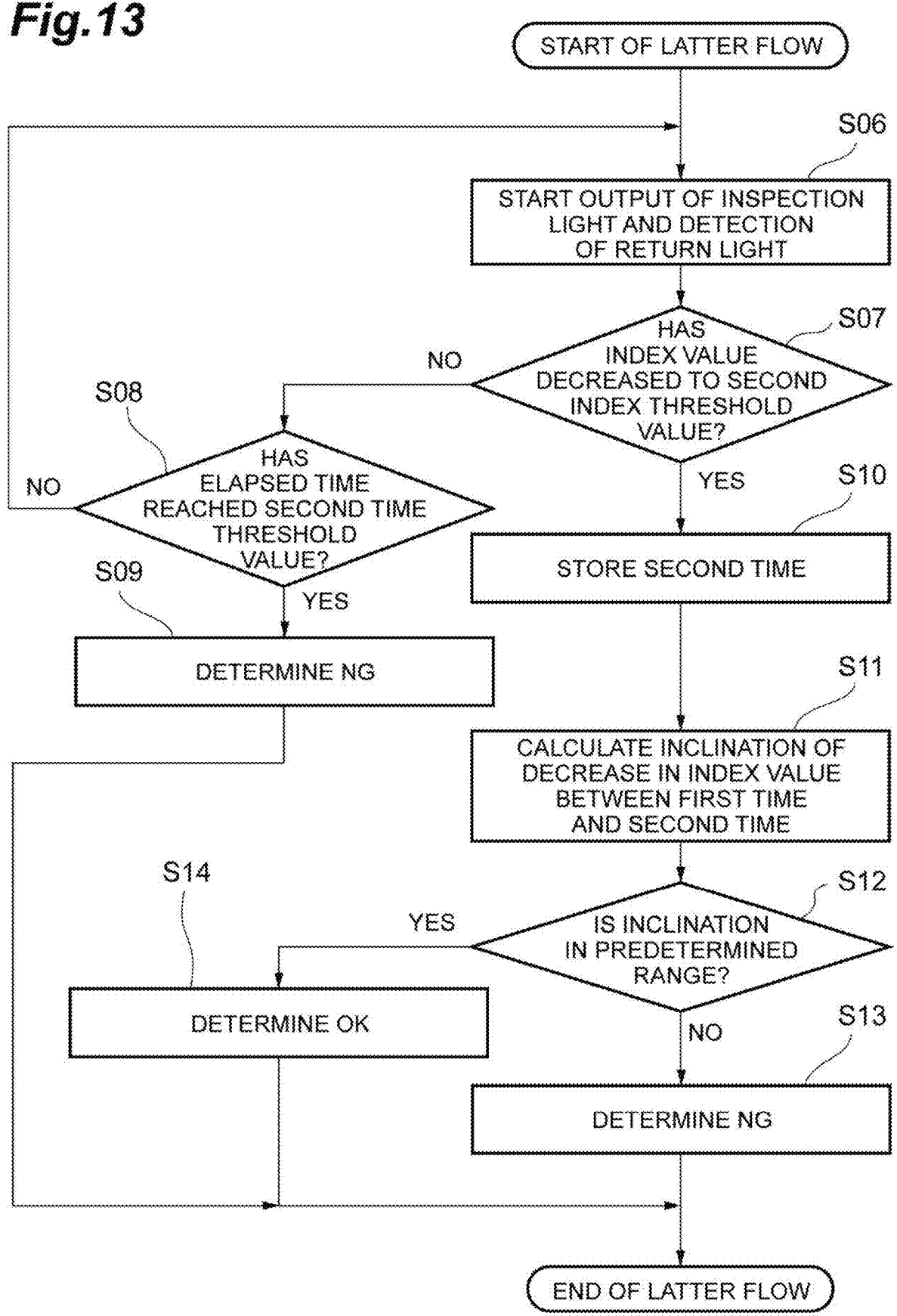
FIG. 13 is a diagram illustrating an example of a latter flow of determination.

FIGS. 12 and 13 are diagrams illustrating an example of the operation of a fermentation state monitoring apparatus. FIG. 12 illustrates an example of the former flow of determination, and FIG. 13 illustrates an example of the latter flow of determination. These flows are repeatedly executed at predetermined intervals, for example, every minute, every ten minutes, and every 60 minutes, after starting the fermentation of the fermented food S. As illustrated in FIG. 12, in the former flow, first, the output of the inspection light Ta and the detection of the return light Tb are performed (step S01). Then, an index value for the fermented food S under fermentation is calculated by the detection of the return light Tb, and the determination unit 56 determines whether or not the calculated index value has decreased to the first index threshold value K1 (step S02).

In a case where it is determined that the index value has not decreased to the first index threshold value K1 in step S02, the determination unit 56 subsequently determines whether or not the elapsed time from the start of fermentation has reached the first time threshold value T1 (step S03). In a case where it is determined that the elapsed time has not reached the first time threshold value T1 in step S03, the processing of steps S01 and S02 is executed again. On the other hand, in a case where it is determined that the elapsed time has reached the first time threshold value T1 in step S03, it is determined that there is an abnormality in the fermentation state of the fermented food (step S04), and the process ends. In a case where it is determined that the index value has decreased to the first index threshold value K1 in step S02, the time when the index value has reached the first index threshold value K1 is stored in the determination unit 56 as a first time t1 (refer to FIG. 11) (step S05).

After step S05, the process proceeds to the latter flow. As illustrated in FIG. 13, also in the latter flow, first, the output of the inspection light Ta and the detection of the return light Tb are performed (step S06). Then, an index value for the fermented food S under fermentation is calculated by the detection of the return light Tb, and the determination unit 56 determines whether or not the calculated index value has decreased to the second index threshold value K2 (step S07). In a case where it is determined that the index value has not decreased to the second index threshold value K2 in step S07, the determination unit 56 subsequently determines whether or not the elapsed time from the start of fermentation has reached the second time threshold value T2 (step S08). In a case where it is determined that the elapsed time has not reached the second time threshold value T2 in step S08, the processing of steps S06 and S07 is executed again.

On the other hand, in a case where it is determined that the elapsed time has reached the second time threshold value T2 in step S08, it is determined that there is an abnormality in the fermentation state of the fermented food (step S09), and the process ends. In a case where it is determined that the index value has decreased to the second index threshold value K2 in step S07, the time when the index value has reached the second index threshold value K2 is stored in the determination unit 56 as a second time t2 (refer to FIG. 11) (step S10). After the second time t2 is stored, the first time t1 stored in step S05 is referred to, and the inclination of decrease in the index value between the first time t1 and the second time t2 is calculated (step S11).

For example, the inclination is calculated by linear approximation of the index value calculated between the first time t1 and the second time t2. Then, the determination unit 56 determines whether or not the inclination is in a predetermined range (step S12). Similar to the index threshold value and the time threshold value, a threshold value for determination of an inclination is set based on the measurement results obtained by measuring a change in index value in a case where fermentation of a fermented food is performed normally multiple times, for example. In a case where it is determined that the inclination is not in a predetermined range in step S12, it is determined that there is an abnormality in the fermentation state of the fermented food (step S13), and the process ends. On the other hand, in a case where it is determined that the inclination is in a predetermined range in step S12, it is determined that the fermentation state of the fermented food is normal (step S14), and the process ends.

[Operational Effect]

As described above, in the fermentation state monitoring apparatuses 1A and 1B, the terahertz wave T is output to the fermented food S under fermentation in the sealed product container P as the inspection light Ta. Since the terahertz wave T passes through the product container P made of, for example, paper or plastic, it is possible to inspect the fermented food in the product container P in a non-destructive manner. In addition, the reflectance of the return light Tb or the absorption coefficient of the return light Tb has a correlation with the pH value of the fermented food S under fermentation. Therefore, the fermentation progress of the fermented food S can be determined in real time by using these parameters as index values.

In addition, in the present embodiment, the frequency of the terahertz wave T is 1 THz or less. In this frequency band, the transmission of the terahertz wave T with respect to the product container P made of paper or plastic can be sufficiently secured. In addition, since the correlation between the index value and the pH value is further strengthened, it is possible to improve the determination accuracy of the fermentation progress.

In addition, in the present embodiment, the determination unit 56 has the first index threshold value K1 for the index value and the first time threshold value T1 for the elapsed time from the start of fermentation. When the elapsed time from the start of fermentation reaches the first time threshold value T1, in a case where the index value has not decreased from the value at the start of fermentation to the first index threshold value K1, the determination unit 56 determines that there is an abnormality in the fermentation state of the fermented food. In this manner, an abnormality in the fermentation state in the early stage of fermentation can be determined.

In addition, in the present embodiment, the determination unit 56 has the second index threshold value K2 set to a value lower than the first index threshold value K1 and the second time threshold value T2 set to a time later than the first time threshold value T1, and determines that there is an abnormality in the fermentation state of the fermented food in a case where the time when the index value has decreased to the second index threshold value K2 exceeds the second time threshold value T2. In this manner, an abnormality in the fermentation state in the late stage of fermentation can be determined.

In addition, in the present embodiment, the first time t1 when the index value has decreased to the first index threshold value K1 and the second time t2 when the index value has decreased to the second index threshold value K2 are stored in the determination unit 56, and it is determined that there is an abnormality in the fermentation state of the fermented food in a case where the inclination of the decrease in the index value between the first time t1 and the second time t2 is not in a predetermined range. In this manner, an abnormality in the progress of the fermentation state can be determined.

In addition, in the present embodiment, the inspection head 71 that guides the inspection light Ta toward the fermented food S and guides the return light Tb toward the terahertz wave detection element 40 is provided. In this case, only the inspection head 71 can be disposed close to the fermented food S placed in the fermentation room 64 or the like. Therefore, it is possible to secure good workability in the case of monitoring a large number of fermented foods S and the like.

Modification Examples

In the embodiment described above, examples of the fermentation state monitoring apparatuses 1A and 1B are illustrated. However, in the apparatuses, the terahertz wave generation element 20 is not limited to that using laser excitation, and may be a direct oscillator, such as a QCL, a Gunn diode, a BWO, or a resonant tunneling diode. In addition, the terahertz wave detection element 40 is not limited to that using detection by laser, and may be a Schottky barrier diode, a Golay cell, a pyro detector, a bolometer, or the like.

Figure 14:
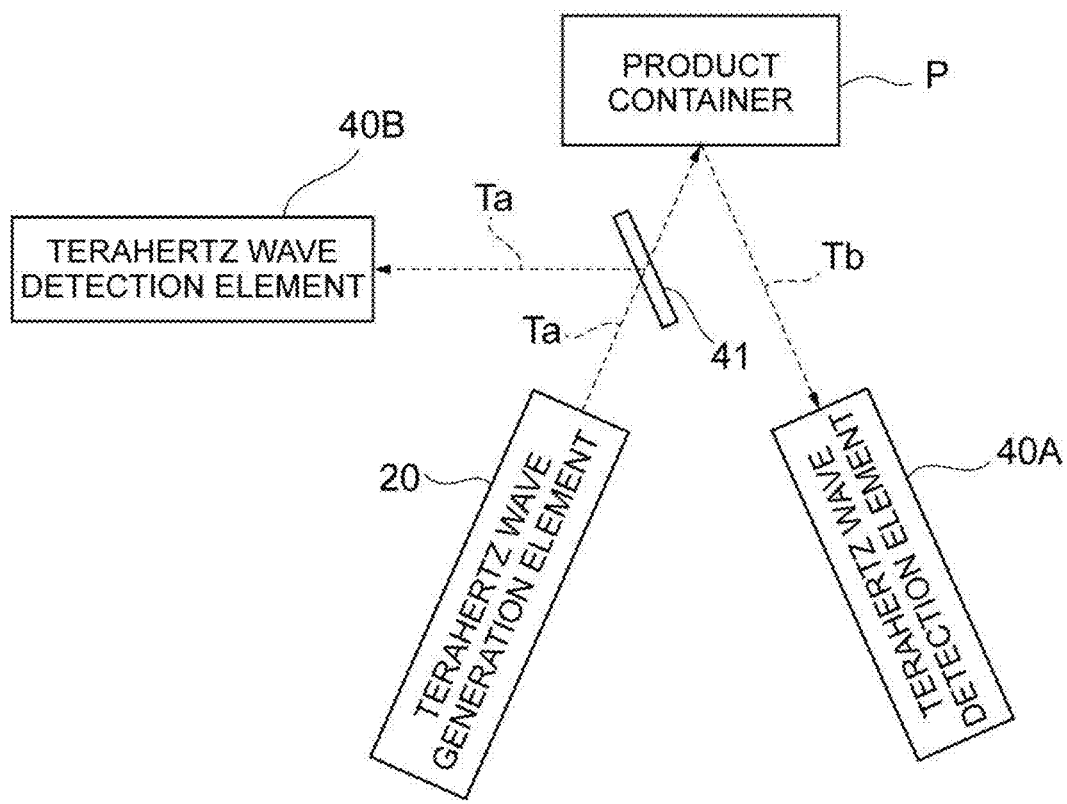
FIG. 14 is a schematic diagram illustrating still another example of the aspect of emission of inspection light.

In addition, as illustrated in FIG. 14, each of the fermentation state monitoring apparatuses 1A and 1B may include a first terahertz wave detection element (first detection unit) 40A that detects the return light Tb and a second terahertz wave detection element (second detection unit) 40B that detects a part of the inspection light Ta. In this case, a part of the inspection light Ta is guided to the second terahertz wave detection element 40B by, for example, a beam splitter 41, and the rest of the inspection light Ta is transmitted through the beam splitter 41 to move toward the product container P and is reflected by the fermented food S in the product container P to become the return light Tb. The difference between the detection signals from the terahertz wave detection elements 40A and 40B is detected by, for example, the differential amplifier 54 as a difference detector. In this case, since the influence of the output drift of the terahertz wave T by the terahertz wave generation element 20 can be eliminated, it is possible to improve the determination accuracy of the fermentation progress.

Figure 15:
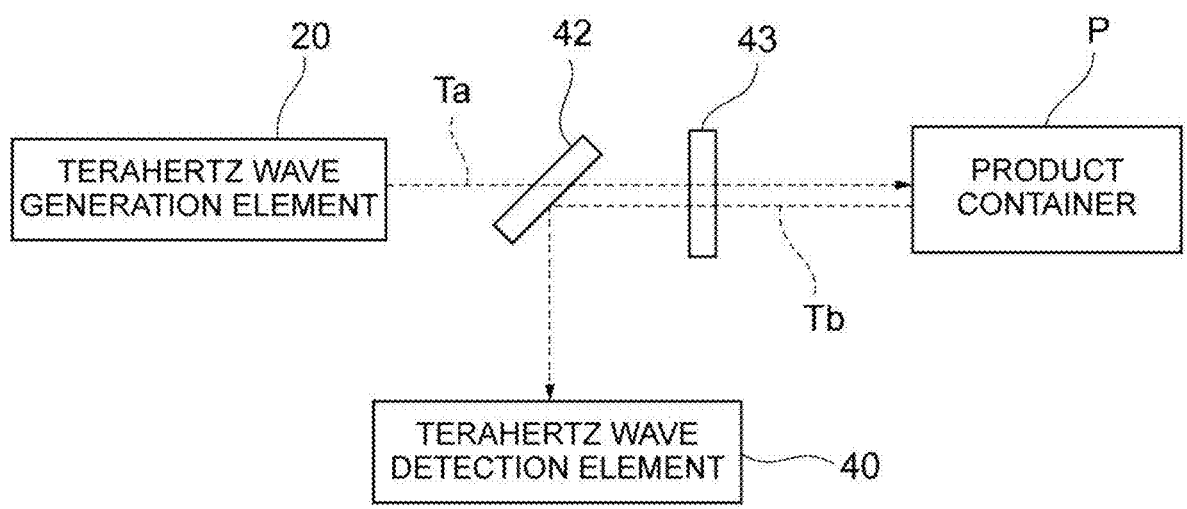
FIG. 15 is a schematic diagram illustrating still another example of the aspect of emission of inspection light.

In addition, from the viewpoint of easily separating the optical paths of the inspection light Ta and the return light Tb from each other, it is preferable that the optical axis of the inspection light Ta with respect to the product container P is inclined with respect to the wall surface of the product container P. In a case where the optical axis of the inspection light Ta with respect to the product container P is perpendicular to the wall surface of the product container P, for example, as illustrated in FIG. 15, it is preferable to dispose a polarizer 42 and a λ/4 wavelength plate 43 on the optical path of the terahertz wave T between the terahertz wave generation element 20 and the product container P. In this case, since the terahertz wave T passes through the λ/4 wavelength plate 43 twice, the polarization of the return light Tb is rotated by 90° with respect to the polarization of the inspection light Ta. Therefore, only the return light Tb can be separated by the polarizer 42 and guided to the terahertz wave detection element 40.

What is claimed is:

1. A fermentation state monitoring apparatus, comprising:
   a terahertz wave output unit that outputs inspection light using a terahertz wave to a fermented food under fermentation in a sealed product container;
   a terahertz wave detection element that detects return light of the inspection light reflected by the fermented food in the product container; and
   a computer processor configured to determine a fermentation progress of the fermented food based on an index value including a reflectance of the return light with respect to the inspection light or an absorption coefficient of the return light with respect to the inspection light,
   wherein a frequency of the terahertz wave is 1 THz or less, and
   wherein the index value is based on one or more changes in the fermented food other than a change in concentration of the fermented food.

2. The fermentation state monitoring apparatus according to claim 1,
   wherein the computer processor is configured to use a first index threshold value for the index value and a first time threshold value for an elapsed time from start of fermentation, and
   when the elapsed time from the start of fermentation reaches the first time threshold value, in a case where the index value has not decreased from a value at the start of fermentation to the first index threshold value, the computer processor is configured to determine that there is an abnormality in a fermentation state of the fermented food.

3. The fermentation state monitoring apparatus according to claim 2,
   wherein the computer processor is configured to use a second index threshold value set to a value lower than the first index threshold value and a second time threshold value set to a time later than the first time threshold value, and
   in a case where a time when the index value has decreased to the second index threshold value exceeds the second time threshold value, the computer processor is configured to determine that there is an abnormality in the fermentation state of the fermented food.

4. The fermentation state monitoring apparatus according to claim 3,
   wherein the computer processor is configured to store a first time when the index value has decreased to the first index threshold value and a second time when the index value has decreased to the second index threshold value, and
   in a case where an inclination of a decrease in the index value between the first time and the second time is not in a predetermined range, the computer processor is configured to determine that there is an abnormality in the fermentation state of the fermented food.

5. The fermentation state monitoring apparatus according to claim 1,
   wherein the terahertz wave detection element includes a first terahertz wave detection element that detects the return light, a second detection element that detects a part of the inspection light, and a difference detection element that detects a difference between a detection signal from the first detection element and a detection signal from the second detection element.

6. The fermentation state monitoring apparatus according to claim 1, further comprising:
   an inspection head that guides the inspection light toward the fermented food.

7. A fermentation state monitoring method, comprising:
   an output step for outputting inspection light using a terahertz wave to a fermented food under fermentation in a sealed product container;

a detection step for detecting return light of the inspection light reflected by the fermented food in the product container; and a determination step for determining a fermentation progress of the fermented food based on an index value including a reflectance of the return light with respect to the inspection light or an absorption coefficient of the return light with respect to the inspection light, wherein a frequency of the terahertz wave is 1 THz or less, and wherein the index value is based on one or more changes in the fermented food other than a change in concentration of the fermented food.

8. The fermentation state monitoring method according to claim 7, wherein, in the determination step, a first index threshold value for the index value and a first time threshold value for an elapsed time from start of fermentation are used, and when the elapsed time from the start of fermentation reaches the first time threshold value, in a case where the index value has not decreased from a value at the start of fermentation to the first index threshold value, it is determined that there is an abnormality in a fermentation state of the fermented food.

9. The fermentation state monitoring method according to claim 8, wherein, in the determination step, a second index threshold value set to a value lower than the first index threshold value and a second time threshold value set to a time later than the first time threshold value are used, and in a case where a time when the index value has decreased to the second index threshold value exceeds the second time threshold value, it is determined that there is an abnormality in the fermentation state of the fermented food.

10. The fermentation state monitoring method according to claim 9, wherein, in the determination step, a first time when the index value has decreased to the first index threshold value and a second time when the index value has decreased to the second index threshold value are stored, and in a case where an inclination of a decrease in the index value between the first time and the second time is not in a predetermined range, it is determined that there is an abnormality in the fermentation state of the fermented food.

11. The fermentation state monitoring method according to claim 7, wherein, in the detection step, detection of the return light and detection of a part of the inspection light are performed, and a difference between a detection result of the return light and a detection result of a part of the inspection light is detected.

12. The fermentation state monitoring method according to claim 7, wherein, in the output step and the detection step, an inspection head that guides the inspection light toward the fermented food is used.

* * * * *